US007354488B2

(12) United States Patent
Klein et al.

(10) Patent No.: US 7,354,488 B2
(45) Date of Patent: Apr. 8, 2008

(54) PALLADIUM ALLOY

(75) Inventors: Arthur S. Klein, Orange, CT (US); Edward F. Smith, III, Madison, CT (US)

(73) Assignee: Deringer-Ney, Inc., Bloomfield, CT (US)

( * ) Notice: Subject to any disclaimer, the term of this patent is extended or adjusted under 35 U.S.C. 154(b) by 0 days.

(21) Appl. No.: 11/125,746

(22) Filed: May 10, 2005

(65) Prior Publication Data

US 2005/0247379 A1 Nov. 10, 2005

Related U.S. Application Data

(60) Provisional application No. 60/569,671, filed on May 10, 2004.

(51) Int. Cl.
*C22C 5/00* (2006.01)

(52) U.S. Cl. .......................... 148/430; 420/463

(58) Field of Classification Search ................ 148/430; 420/463–465
See application file for complete search history.

(56) References Cited

U.S. PATENT DOCUMENTS

| | | |
|---|---|---|
| 1,990,277 A | 2/1935 | Feussner et al. |
| 2,478,225 A | 8/1949 | Atkinson |
| 4,124,382 A | 11/1978 | Prosen |
| 4,387,072 A | 6/1983 | Schaffer |
| 4,518,564 A | 5/1985 | Prasad |
| 4,576,789 A | 3/1986 | Proasad |
| 4,619,810 A | 10/1986 | Praqsad |
| 4,992,297 A * | 2/1991 | van der Zel ............... 427/2.27 |
| 5,011,311 A | 4/1991 | Harris et al. |
| 5,431,875 A | 7/1995 | Cameron et al. |
| 5,462,437 A | 10/1995 | Prasad et al. |
| 5,484,569 A | 1/1996 | Klein et al. |
| 5,518,556 A | 5/1996 | Weber et al. |
| 5,916,518 A | 6/1999 | Chesnes |
| 6,764,561 B1 | 7/2004 | Miles et al. |
| 2005/0230009 A1 | 10/2005 | Miles et al. |

OTHER PUBLICATIONS

ASM vol. 2 Properties and Selection: Nonferrous Alloys and Special-Purpose Materials, "Palladium and Palladium Alloys", ASM International, 2002, p. 1-10.*

* cited by examiner

*Primary Examiner*—Roy King
*Assistant Examiner*—Janelle Morillo
(74) *Attorney, Agent, or Firm*—Schiff Hardin LLP

(57) ABSTRACT

A family of alloys for use in medical, electrical contact and jewelry applications includes as primary components palladium, and boron and at least one of ruthenium, rhenium, platinum, gold, zirconium, tungsten, cobalt, nickel, tantalum and iridium. An alternative embodiment includes palladium and rhenium and/or ruthenium with an additional element iridium, platinum, tungsten, boron, gold, zirconium, cobalt, nickel and tantalum. The present alloy family has a high strength, high radio opacity, and biocompatibility characteristics, while also being workable into various configurations. Where required, some of the alloys also offer post form, heat treatment (age hardening) capabilities for even higher hardness and strength levels.

3 Claims, 15 Drawing Sheets

60 KV Radiograph
(Background lightened to show location of stainless steel sample)

50 KV Radiograph

60 KV Radiograph
(Background lightened to show location of stainless steel sample)

Figure 3  Low Cost Palladium Alloy Development

| alloy # | Pd | Ru | put up B | Ir | Re | Pt | W | Au | Zr | Co | at 50 % CW UTS | % el | hard | Severe Edge cracking |
|---|---|---|---|---|---|---|---|---|---|---|---|---|---|---|
| 844 | 99.65 | | | | | | | | | | 67 | 0.2 | 176 | no |
| 845 | 98.15 | 1.5 | 0.35 | | | | | | | | 89 | 1.1 | 222 | no |
| 846 | 95.5 | 4.5 | | | | | | | | | 108 | 0.6 | 248 | no |
| 849 | 95.45 | 4.5 | 0.05 | | | | | | | | 121 | 0.8 | 303 | no |
| 850 | 95.43 | 4.5 | 0.075 | | | | | | | | 107 | 0.6 | 267 | no |
| 851 | 95.4 | 4.5 | 0.1 | | | | | | | | 107 | 0.7 | 280 | no |
| 852 | 95.3 | 4.5 | 0.2 | | | | | | | | 123 | 0.7 | 309 | no |
| 825 | 95.2 | 4.5 | | | | | | | | | 108 | 0.3 | | no |
| 847 | 95.15 | 4.5 | 0.35 | | | | | | | | 114 | 1.3 | 286 | no |
| 826 | 95.05 | 4.5 | 0.15 | | | | | | | | 137 | 0.8 | | no |
| 853 | 94.8 | 4.5 | 0.7 | | | | | | | | 143 | 1.1 | 389 | yes |
| 822 | 94.5 | 5.5 | | | | | | | | | 104 | 0.9 | | yes |
| 854 | 94.5 | 4.5 | 1 | | | | | | | | 126 | 0.1 | 308 | yes |
| 858 | 94.15 | 4.5 | 0.35 | | 1 | | | | | | 127 | 1 | 291 | no |
| 863 | 94.15 | 4.5 | 0.35 | | | | | | | | 109 | 0.2 | 291 | no |
| 864 | 94.15 | 4.5 | 0.35 | | | | | | 1 | | 121 | 0.6 | 292 | no |
| 855 | 94 | 4.5 | 1.5 | | | | | | | | 114 | 0.1 | 435 | yes |
| 848 | 93.15 | 6.5 | 0.35 | | | | | | | | 118 | 1.1 | 292 | yes |
| 827 | 93.05 | 4.5 | 0.15 | | 0.3 | | | | | | 122 | 0.8 | | no |
| 812 | 92.5 | 7.5 | | | | | | | | | | | | no |
| 820 | 92.5 | 4.5 | | 3 | | 2 | | | | | 131 | 0.5 | | no |
| 859 | 92.15 | 4.5 | 0.35 | 3 | | | | | | | 128 | 0.7 | 311 | yes |
| 856 | 91.65 | 8 | 0.35 | | | | 0.8 | | | | | | 286 | yes |
| 821 | 91.5 | 5.5 | | 3 | | | | | | | | | | yes |
| 811 | 90.5 | 4.5 | 1.5 | 0.5 | | 4.5 | | | | | 106 | 0.5 | 243 | yes |
| 857 | 89.65 | 10 | 0.35 | | | 10 | | | | | | | >482 | yes |
| 860 | 85.15 | 4.5 | 0.35 | | 0.3 | 9.2 | | | | | 122 | 0.4 | 303 | no |
| 861 | 85.15 | 4.5 | 0.35 | | | | 1.2 | | | | 135 | 1.1 | 328 | no |
| 862 | 85.15 | 4.5 | 0.35 | | | 15 | | | | | 111 | 1 | 266 | no |
| 877 | 96.35 | 3 | 0.35 | | | 15 | | | | | | | | |
| 879 | 80.15 | 4.5 | 0.35 | | 0.3 | 13.8 | 1.2 | | | | | | | |
| 880 | 79.85 | 4.5 | 0.35 | | | 13.8 | 1.2 | | | | | | | |
| 881 | 80.15 | 4.5 | 0.35 | | 0.3 | 10 | | | | | | | | |
| 882 | 79.85 | 4.5 | 0.35 | | | 10 | | 10 | | | | | | |
| 885 | 83.65 | 6 | 0.35 | | 2.5 | | | | | | | | | |
| 886 | 81.15 | 6 | 0.35 | | 5 | | | | | | | | | |
| 883 | 90.15 | 4.5 | 0.35 | | | | | | | | | | | |
| 884 | 70.15 | 4.5 | 0.35 | | | 25 | | | | | | | | |

Figure 4

Series VI & VII Stress Relieve Anneal Tests

Hardness, HK(100) vs. Anneal Temperature

| PE # | % CW | CW | Annealing Temperature, °C for 1 minute | | | | | | |
|---|---|---|---|---|---|---|---|---|---|
| | | | 450 | 500 | 550 | 600 | 700 | 750 | |
| 860 | 50 | 303 | 315 | 311 | 303 | | | | |
| | 58 | 435 | 433 | 371 | 409 | | | | |
| 862 | 50 | 266 | 275 | 277 | 271 | | | | |
| | 73 | 381 | 399 | 352 | 360 | | | | |
| 863 | 50 | 291 | 302 | 288 | 295 | | | | |
| | 67 | 397 | 417 | 298 | 366 | | | | |
| 864 | 50 | 292 | 282 | 283 | 272 | | | | |
| | 73 | 386 | 378 | 378 | 369 | | | | |
| 877 | 50 | 264 | 277 | 253 | 256 | | | | |
| | 75 | 380 | 375 | 350 | 329 | | | | |
| 879 | 50 | 337 | 331 | 320 | 350 | | | | |
| | 69 | 456 | 455 | 437 | 433 | | | | |
| 880 | 50 | 338 | 365 | 348 | 345 | 371 | 360 | 343 | |
| | 67 | 333 | 465 | 451 | 443 | 451 | 419 | 429 | |
| 881 | 50 | 334 | 374 | 393 | 386 | 375 | 371 | 350 | |
| | 66 | 433 | 468 | 450 | 450 | 438 | 443 | 431 | |
| 882 | 50 | 325 | 368 | 378 | 384 | 377 | 368 | 350 | |
| | 69 | 439 | 491 | 472 | 457 | 465 | 453 | 444 | |
| 883 | 50 | 367 | 414 | 404 | 415 | 418 | 338 | 395 | |
| | 66 | 449 | 503 | 476 | 462 | 461 | 459 | 461 | |
| 884 | 50 | 395 | 422 | 405 | 402 | | | | |
| | 68 | 487 | 488 | 461 | 441 | | | | |
| 885 | 50 | 334 | 311 | 320 | 320 | | | | |
| | 68 | 445 | 418 | 443 | 414 | | | | |
| 886 | 50 | 370 | 407 | 391 | 406 | | | | |
| | 69 | 507 | 279 | 499 | 431 | | | | |

Figure 5

Strip vs. Wire Properties

| Alloy (Composition) | Condition (Size) | UTS (ksi) | 0.2% YS (ksi) | Elongation (%) |
|---|---|---|---|---|
| PE-852 Strip (95.3 Pd, 4.5 Ru, 0.2 B) | 50% CW (.009") | 122.6 | 117.7 | 0.7 |
| PE-852-2 Wire (95.3 Pd, 4.5 Ru, 0.2 B) | 48% CW (.095") | 149.0 | --- | <0.5 |
| | 40% CW +SR (.102") | 134.5 | --- | 8.8 |

Notes:
- Compositions as put-up + additional 5% Boron, e.g. 0.21%
- Stress Relief Anneal (SR): 1350°F / 1.5 min. / Air / WQ
- Gage Lengths: Strip = 2"
  Wire = 0.5"

Figure 6
Series I – IV Strip Test Results

| Series | Alloy (Composition) | Condition (Size) | UTS (ksi) | 0.2% YS (ksi) | Elongation (% in 2") | Hardness (HK) | Edge Rating |
|---|---|---|---|---|---|---|---|
| | Target Properties ⇒ | For Wire (0.005" / 0.010") | 140-185 | | 2.5 min. | | |
| IS | PE-799 (90 Pd / 10 Ir) | 44% Cold Worked (.009") | 81.7 | 80.4 | 0.89 | | |
| | | 69% Cold Worked (.005") | 82.5 | 80.9 | 0.84 | | |
| IIS | PE-811 (4.5Pt / 90.5Pd / 4.5Ru / 0.5Ir) | 50% Cold Worked (0.009") | 106.4 | 106.2 | 0.5 | 243 | |
| | | 75% Cold Worked (0.008") | 112.4 | 110.6 | 0.8 | 259 | |
| IIIS | PE-812 (92.5Pd / 7.5Ru) | Brittle | | | | | |
| | | Brittle | | | | | |
| IIS | PE-807 (95.5Pd / 4.5Ru) | 50% Cold Worked (0.009") | 110.8 | | 0.2 | 296 | |
| | | 75% Cold Worked (0.008") | 132.6 | 132.2 | 0.3 | 298 | |
| Series IV | PE-820 (92.5Pd / 4.5Ru / 3 Ir) | 50% Cold Worked (0.009") | 130.5 | 114.6 | 0.5 | 280 | 3 |
| | | 73% Cold Worked (0.009") | 146.9 | 127.2 | 0.4 | 325 | 3 |
| | PE-822 (94.5Pd / 5.5Ru) | 50% Cold Worked (0.009") | 103.7 | 101.6 | 0.9 | | 2 |
| | | 75% Cold Worked (0.008") | 106.4 | 105.1 | 0.5 | | 2 |
| | PE-821 (91.5Pd / 5.5Ru / 3Ir) | Brittle | | | | | 4 |
| | | Brittle | | | | | 4 |
| | PE-825 (95.2Pd / 4.5Ru / 0.3Re) | 50% Cold Worked (0.009") | 107.9 | 106.9 | 0.3 | 277 | 1 |
| | | 75% Cold Worked (0.008") | 108.8 | 107.0 | 0.6 | 271 | 2 |
| | PE-826 (95.05Pd / 4.5Ru / 0.3Re / 0.15B) | 50% Cold Worked (0.009") | 136.6 | 130.4 | 0.8 | 339 | 2 |
| | | 73% Cold Worked (0.009") | 172.3 | 153.5 | 1.3 | 414 | 2 |
| | PE-827 (93.05Pd / 4.5Ru / 2 Pt / 0.3Re/ .15B ) | 50% Cold Worked (0.009") | 122.1 | 118.2 | 0.8 | 295 | 2 |
| | | 71% Cold Worked (0.0095") | 157.3 | 144.9 | 0.8 | 402 | 1 |

- For comparison, pure Pd @ 50% C.W. has UTS of ≈ 45 ksi
- Boron containing alloys put-up @ 0.35%
- Processed using router Medtronic Strip Router.doc 11-4-03
- Edge Rating: 1 = Best, 4 = Worst

Figure 7

Low Cost Palladium Alloy
Series IV Strip Test Results – Stress Relieved

| Alloy | Condition (Size) | UTS (ksi) | 0.2% YS (ksi) | Elong. (% in 2") |
|---|---|---|---|---|
| Target Properties ⇒ | For Wire (0.005" / 0.010") | 140-185 | ----- | 2.5 min. |
| PE-820 | 50% CW | 130.5 | 114.6 | 0.5 |
|  | 73% CW | 146.9 | 127.2 | 0.4 |
| PE-821 | Brittle | --- | --- | --- |
| PE-822 | 50% CW | 103.7 | 101.6 | 0.9 |
|  | SR 500°C / 1 min / Box Furn. | 101.6 | 99.3 | 1.5 |
|  | SR 600°C / 1 min / Box Furn. | 96.6 | 92.8 | 2.4 |
|  | SR 750°C / 1 min / Box Furn. | 95.2 | 83.2 | 7.3 |
|  | 75% CW | 106.4 | 105.1 | 0.5 |
|  | SR 500°C / 1 min / Box Furn. | 104.0 | 101.2 | 2.3 |
|  | SR 600°C / 1 min / Box Furn. | 101.2 | 97.7 | 3.0 |
|  | SR 750°C / 1 min / Box Furn. | 101.7 | 91.1 | 6.8 |
| PE-825 | 50% CW | 107.9 | 106.9 | 0.3 |
|  | 75% CW | 108.8 | 107.0 | 0.6 |
| PE-826 | 50% CW | 136.6 | 130.4 | 0.8 |
|  | SR 500°C / 1 min / Box Furn. | 130.3 | 116.5 | 8.0 |
|  | SR 600°C / 1 min / Box Furn. | 123.5 | 107.1 | 11.0 |
|  | 73% CW | 172.3 | 153.5 | 1.3 |
|  | SR 500°C / 1 min / Box Furn. | 154.5 | 135.0 | 5.6(JB) |
|  | SR 600°C / 1 min / Box Furn. | 150.0 | 131.2 | 5.6(JB) |
| PE-827 | 50% CW | 122.1 | 118.2 | 0.8 |
|  | SR 500°C / 1 min / Box Furn. | 112.6 | 101.6 | 6.7 |
|  | SR 600°C / 1 min / Box Furn. | 113.0 | 100.4 | 8.9 |
|  | SR 750°C / 1 min / Box Furn. | 100.0 | 83.0 | 9.1 |
|  | 71% CW | 157.3 | 144.9 | 0.8 |
|  | SR 450°C / 1 min / Box Furn. | 156.7 | 143.1 | 6.5 |
|  | SR 500°C / 1 min / Box Furn. | 155.0 | 136.1 | 8.8 |
|  | SR 550°C / 1 min / Box Furn. | 150.4 | 128.2 | 10.6 |
|  | SR 600°C / 1 min / Box Furn. | 146.9 | 128.6 | 8.0 |
|  | SR 750°C / 1 min / Box Furn. | 129.0 | 109.8 | 6.3 |

Figure 8
Low Cost Palladium Alloy
Series V Strip Test Results

| Alloy (Composition) | Condition (Size) | UTS (ksi) | 0.2% YS (ksi) | Elongation (% in 2") | Hardness (HK100) | Edge Condition |
|---|---|---|---|---|---|---|
| Target Properties ⇒ | For Wire (0.005" / 0.010") | 140-185 | | 2.5 min. | | |
| PE-844 (99.65 Pd, 0.35 B) | 50% CW (.009") | 67.4 | 60.9 | 0.2 | 176 | 1 |
| PE-845 (98.15 Pd, 1.5 Ru, 0.35 B) | 50% CW (.009") | 88.7 | 87.1 | 1.1 | 222 | 1 |
| PE-846 (95.5 Pd, 4.5 Ru) | 50% CW (.009") | 107.5 | 104.3 | 0.6 | 248 | 1 |
| PE-847 (95.15 Pd, 4.5 Ru, 0.35 B) | 50% CW (.009") | 113.6 | 106.2 | 1.3 | 286 | 2 |
| PE-848 (93.15 Pd, 6.5 Ru, 0.35 B) | 50% CW (.009") | 118.3 | 112.0 | 1.1 | 292 | 3 |
| PE-849 (95.45 Pd, 4.5 Ru, 0.05 B) | 50% CW (.009") | 121.0 | 115.8 | 0.8 | 303 | 1 |
| PE-850 (95.425 Pd, 4.5 Ru, 0.075 B) | 50% CW (.009") | 107.1 | 104.4 | 0.6 | 267 | 1 |
| PE-851 (95.4 Pd, 4.5 Ru, 0.1 B) | 50% CW (.009") | 106.6 | 102.4 | 0.7 | 280 | 1 |
| PE-852 (95.3 Pd, 4.5 Ru, 0.2 B) | 50% CW (.009") | 122.6 | 117.7 | 0.7 | 309 | 1 |
| PE-853 (94.8 Pd, 4.5 Ru, 0.7 B) | 50% CW (.009") | 142.7 | 133.1 | 1.1 | 389 | 4 |

- Tensile problems-many jaw breaks.
- For comparison, pure Pd @ 50% C.W. has UTS of ≈ 35 ksi
- Boron containing alloys put-up @ +5%
- Processed using router Medtronics V Strip Router.doc 2-12-04.
- Edge Condition Rating:  1 = No flaws, 2 = Minor flaws only, 3 = Many minor flaws only, 4 = Major flaws

Figure 9
Series VI Strip Test Results

| Alloy (Composition) | Condition (Size) | UTS (ksi) | 0.2% YS (ksi) | Elongation (% in 2") | Hardness HK100 | Edge Condition |
|---|---|---|---|---|---|---|
| Target Properties ⇒ | For Wire (0.005"/ 0.010") | 140-185 | ---- | 2.5 min. | ---- | |
| PE-854 | 50% CW (.009") | 126.0 | 123.5 | 0.1 | 308 | 3 |
| (94.5 Pd, 4.5 Ru 1.0 B) | 52% CW (.016") | 186.4 | 184.9 | 1.3 | 485 | 3 |
| PE-855 | 50% CW (.010") | 113.9 | 0.0 | 0.1 | 435 | 4 |
| (94.0 Pd, 4.5 Ru, 1.5 B) | 52% CW (.016") | ---- | ---- | ---- | 486 | 4 |
| PE-856 | 50% CW (.008") | ---- | ---- | ---- | 286 | 4 |
| (91.65 Pd, 8.0 Ru,.35 B) | 64% CW (.012") | ---- | ---- | ---- | 397 | 4 |
| PE-857 | | | | | | |
| (89.65 Pd, 10.0 Ru, 0.35 B) | 25% CW (.140") | ---- | ---- | ---- | 482 | 4 |
| PE-858 | 50% CW (.009") | 127.4 | 121.6 | 1.0 | 291 | 1 |
| (94.15 Pd, 4.5 Ru, 1.0 Re, 0.35 B) | 61% CW (.013") | 168.0 | 156.8 | 0.7 | 388 | 1 |
| PE-859 | 50% CW (.007") | 128.0 | 103.8 | 0.7 | 311 | 4 |
| (92.15 Pd, 4.5 Ru, 3.0 Ir, 0.35 B) | 52% CW (.016") | 192.3 | 185.6 | 0.5 | 408 | 4 |
| PE-860 | 50% CW (.008") | 122.2 | 116.8 | 0.4 | 303 | 1 |
| (85.15 Pd, 4.5 Ru, 10.0 Pt, 0.35 B) | 58% CW (.014") | 184.4 | 174.2 | 1.0 | 435 | 2 |
| PE-861 | 50% CW (.008") | 135.0 | 127.6 | 1.1 | 328 | 1 |
| (85.15 Pd, 4.5 Ru,9.2 Pt, 0.35 B ,.8 W) | 61% CW (.013") | 180.3 | 175.7 | 0.1 | 434 | 2 |
| PE-862 | 50% CW (.008") | 111.2 | 107.5 | 1.0 | 266 | 2 |
| (85.15 Pd, 4.5 Ru, 0.35 B, 10.0 Au) | 73% CW (.009") | 166.4 | 88.9 | 1.0 | 381 | 3 |
| PE-863 | 50% CW (.008") | 108.7 | 92.4 | 0.2 | 291 | 2 |
| (94.15 Pd, 4.5 Ru, 0.35 B, 1.0 Zr) | 67% CW (.011") | 172.0 | 159.1 | 0.8 | 397 | 2 |
| PE-864 | 50% CW (.009") | 121.4 | 116.1 | 0.6 | 292 | 1 |
| (94.15 Pd, 4.5 Ru, 0.35 B, 1.0 Co) | 73% CW (.009") | 160.8 | 152.6 | 0.8 | 386 | 1 |

- Tensile problems-many jaw breaks.
- For comparison, pure Pd @ 50% C.W. has UTS of ≈ 35 ksi
- Boron containing alloys put-up @ +5%
- Processed using router Medtronics VI Strip Router.doc 3-09-04
- Edge Condition Rating: 1=No flaws, 2=Minor flaws only, 3=Many minor flaws, 4= Major Flaws

Figure 10
Series VII Strip Test Results

| Alloy (Composition) Target Properties ⇒ | Condition (Size) For Wire (0.005"/ 0.010") | UTS (ksi) 140-185 | 0.2% YS (ksi) ---- | Elongation (% in 2") 2.5 min. | Hardness HK100 ---- | Edge Condition |
|---|---|---|---|---|---|---|
| PE-877 (96.35 Pd, 3.0 Ru, .35 B, 0.3 Re) | 50% CW (.009") | 127.8 | 94.0 | 0.2 | 264 | 1 |
|  | 75% CW (.008") | 177.5 | 141.3 | 0.8 | 380 | 1 |
| PE-879 (80.15 Pd,15.0 Pt, 4.5 Ru, 0.35 B) | 50% CW (.009") | 134.1 | 132.7 | 0.1 | 337 | 1 |
|  | 69% CW (.0103") | 172.6 | 152.8 | 1.0 | 456 | 1 |
| PE-880 (79.85 Pd,15.0 Pt, 4.5 Ru, .35 B, .3 Re) | 50% CW (.009") | 140.6 | 136.9 | 0.8 | 338 | 1 |
|  | 67% CW (.0108") | 182.0 | 163.6 | 0.8 | 333 | 1 |
| PE-881 (80.15 Pd,13.8 Pt,4.5 Ru,.35 B,1.2 W) | 50% CW (.009") | 150.0 | 149.4 | 0.1 | 334 | 1 |
|  | 66% CW (.0113") | 192.7 | 169.7 | 0.9 | 433 | 1 |
| PE-882 (79.85 Pd, 13.8 Pt, 4.5 Ru, .3 Re, 0.35 B, 1.2 W) | 50% CW (.009") | 140.9 | 137.6 | 0.1 | 325 | 1 |
|  | 69% CW (.0102") | 191.1 | 164.9 | 1.2 | 439 | 1 |
| PE-883 (90.15 Pd, 4.5 Ru, 5.0 Re, 0.35 B) | 50% CW (.009") | 161.0 | 153.2 | 0.1 | 367 | 1 |
|  | 66% CW (.0113") | 186.2 | 168.4 | 0.5 | 449 | 1 |
| PE-884 (70.15 Pd, 4.5 Ru, 25.0 Pt, 0.35 B) | 50% CW (.009") | 149.0 | 146.4 | 0.7 | 395 | 4 |
|  | 68% CW (.0106") | 203.0 | ---- | 0.1 | 487 | 4 |
| PE-885 (83.65 Pd, 6.0 Ru,10.0 Pt, 0.35 B,) | 50% CW (.009") | 121.7 | 116.1 | 0.6 | 334 | 4 |
|  | 68% CW (.0106") | 167.1 | 144.8 | 0.5 | 445 | 4 |
| PE-886 (81.15 Pd, 6.0 Ru, 0.35 B, 10.0 Pt, 2.5 Re) | 59% CW (.00725") | 140.2 | ---- | 0.1 | 370 | 4 |
|  | 69% CW (.0102") | ---- | ---- | ---- | 507 | 4 |

- Tensile problems-many jaw breaks.
- For comparison, pure Pd @ 50% C.W. has UTS of ≈ 35 ksi
- Boron containing alloys put-up @ +5%, e.g. 0.368%
- Processed using router Medtronics VII Strip Router.doc 4-6-04
- Edge Condition Rating: 1=No flaws, 2=Minor flaws only, 3=Many minor flaws, 4= Major Flaws

Figure 11

Series VIII – Strip Test Results – B + Re Effects

| Alloy / Composition | % CW | Hardness, HK(100) CW | Hardness, HK(100) SRA 450°C / 1 min. | Edge Rating |
|---|---|---|---|---|
| PE-883 (Pd 90.15, Ru 4.5, Re 5.0, B 0.35) | 62 | 495 | 483 | 1 |
| PE-887 (Pd 95, Re 5) | 77 | 244 | 244 | 1 |
| 888 (Pd 90.5, Ru 4.5, Re 5) | 72 | 286 | 301 | 1 |
| PE-889 (Pd 94.65, Re 5, B 0.35) | 74 | 415 | 405 | 1 |
| PE-890 (Pd 85.15, Ru 4.5, Re 10, B 0.35) | 43 | 571 | 548 | 4 |
| PE-891 (Pd 84.65, Re 15, B 0.35) | 60 | 540 | 530 | 1 |
| PE-892 (Pd 88.15, Ru 1.5, Re 10, B 0.35) | 67 | 504 | 498 | 1 |
| PE-893 (Pd 89.65, Re 10, B 0.35) | 69 | 494 | 482 | 1 |
| PE-894 (Pd 80.15, Ru 4.5, Re 5, B 0.35, Pt 10) | 65 | 544 | 532 | 1 |

Notes:
Edge Rating: 1= Best, 4 = Worst

Figure 12

Radiopacity Data

Summary of Radiographic Data
(densitometer readings)

| Alloy | 50 Kv | 60 Kv | 70 Kv |
|---|---|---|---|
| Stainless steel | .66 | 2.17 | 3.28 |
| Alloy 847 | .20 | .25 | .72 |
| Alloy 879 | .20 | .23 | .62 |
| Alloy 883 | .20 | .24 | .66 |
| 90Pt-10Ir | .20 | .22 | .39 |

Figure 13A

| Alloy Code | Put-Up Composition, wt % | | | | | | | | | | | % CW | Edge* Cond. | Hardness | | | UTS ksi |
| --- | --- | --- | --- | --- | --- | --- | --- | --- | --- | --- | --- | --- | --- | --- | --- | --- | --- |
| | Pd | Re | Ru | B | Pt | Ir | W | Au | Zr | Co | Ni | | | Hard. HK(100) | change with B addition | | |
| PE-924 | 100.00 | | | | | | | | | | | 75 | 1 | 134 | | | 51 |
| PE-925 | 99.65 | | | 0.35 | | | | | | | | 75 | 1 | 270 | 136 | | 98 |
| PE-887 | 95.00 | 5.00 | | | | | | | | | | 75 | 1 | 265 | | | 105 |
| PE-889 | 94.65 | 5.00 | | 0.35 | | | | | | | | 75 | 1 | 398 | 133 | | 146 |
| PE-897 | 90.00 | 10.00 | | | | | | | | | | 75 | 2 | 319 | | | 137 |
| PE-893 | 89.65 | 10.00 | | 0.35 | | | | | | | | 75 | 1 | 477 | 158 | | 191 |
| PE-899 | 85.00 | 15.00 | | | | | | | | | | 75 | 3 | 391 | | | 150 |
| PE-891 | 84.65 | 15.00 | | 0.35 | | | | | | | | 72 | 3 | 537 | 146 | | 230 |
| PE-928 | 80.00 | 20.00 | | | | | | | | | | 70 | 4 | 452 | | | 191 |
| PE-930 | 79.65 | 20.00 | | 0.35 | | | | | | | | 70 | 4 | 585 | 133 | | |
| PE-932 | 99.50 | | 0.50 | | | | | | | | | 75 | 1 | 159 | | | 60 |
| PE-937 | 99.15 | | 0.50 | 0.35 | | | | | | | | 75 | 1 | 284 | 125 | | 102 |
| PE-933 | 99.00 | | 1.00 | | | | | | | | | 75 | 1 | 166 | | | 65 |
| PE-938 | 98.65 | | 1.00 | 0.35 | | | | | | | | 75 | 1 | 328 | 162 | | 124 |
| PE-934 | 98.00 | | 2.00 | | | | | | | | | 75 | 1 | 178 | | | 69 |
| PE-939 | 97.65 | | 2.00 | 0.35 | | | | | | | | 75 | 1 | 369 | 191 | | 136 |
| PE-935 | 96.00 | | 4.00 | | | | | | | | | 75 | 1 | 208 | | | 85 |
| PE-917 | 95.65 | | 4.00 | 0.35 | | | | | | | | 75 | 2 | 423 | 215 | | 170 |
| PE-936 | 92.00 | | 8.00 | | | | | | | | | 75 | 4 | 318 | | | 141 |
| PE-858 | 91.65 | | 8.00 | 0.35 | | | | | | | | 75 | 4 | 495 | 177 | | 193 |
| PE-941 | 89.00 | 10.00 | 1.00 | | | | | | | | | 75 | 1 | 329 | | | 141 |
| PE-950 | 88.65 | 10.00 | 1.00 | 0.35 | | | | | | | | 67 | 2 | 463 | 134 | | 208 |
| PE-942 | 83.00 | 15.00 | 2.00 | | | | | | | | | 75 | 3 | 398 | | | 185 |
| PE-952 | 82.65 | 15.00 | 2.00 | 0.35 | | | | | | | | 50 | 4 | 362 | na | | |

◯ Note- Work Hardening level too high to allow continued processing without intermediate anneal

Figure 13B

| Alloy Code | Put-Up Composition, wt % | | | | | | | | | | | | %CW | Edge* Cond. | Hardness | | | UTS ksi |
|---|---|---|---|---|---|---|---|---|---|---|---|---|---|---|---|---|---|---|
| | Pd | Re | Ru | B | Pt | Ir | W | Au | Zr | Co | Ni | | | Hard. HK(100) | change with B addition | | |
| PE-957 | 80.00 | 10.00 | | | | | | | | | 10.00 | 75 | 2 | 402 | | 176 |
| PE-958 | 79.65 | 10.00 | | 0.35 | | | | | | | 10.00 | 75 | 3 | 485 | 83 | 192 |
| PE-959 | 86.00 | | 4.00 | | | | | | | | 10.00 | 75 | 3 | 393 | | 174 |
| PE-960 | 85.65 | | 4.00 | 0.35 | | | | | | | 10.00 | 75 | 4 | 458 | 65 | |
| PE-961 | 76.00 | 10.00 | 4.00 | | | | | | | | 10.00 | (50) | 4 | 430 | | |
| PE-962 | 75.65 | 10.00 | 4.00 | 0.35 | | | | | | | 10.00 | 75 | 4 | 452 | 22 | 198 |
| PE-964 | 80.00 | 10.00 | | | 10.00 | | | | | | | 75 | 1 | 347 | | 149 |
| PE-965 | 79.65 | 10.00 | | 0.35 | 10.00 | | | | | | | 75 | 4 | 503 | 156 | 214 |
| PE-966 | 86.00 | | 4.00 | | 10.00 | | | | | | | 75 | 2 | 266 | | 107 |
| PE-967 | 85.65 | | 4.00 | 0.35 | 10.00 | | | | | | | 75 | 1 | 385 | 119 | 169 |
| PE-968 | 76.00 | 10.00 | 4.00 | | 10.00 | | | | | | | 75 | 4 | 391 | | 173 |
| PE-969 | 75.65 | 10.00 | 4.00 | 0.35 | 10.00 | | | | | | | (50) | 4 | 586 | 195 | |
| PE-971 | 80.00 | 10.00 | | | | | | | 10.00 | | | (72) | 2 | 518 | | 219 |
| PE-972 | 79.65 | 10.00 | | 0.35 | | | | | 10.00 | | | 75 | 4 | 552 | 36 | 181 |
| PE-973 | 86.00 | | 4.00 | | | | | | 10.00 | | | 75 | 4 | 468 | | 161 |
| PE-974 | 85.65 | | 4.00 | 0.35 | | | | | 10.00 | | | (72) | 4 | 525 | 57 | 192 |
| PE-975 | 76.00 | 10.00 | 4.00 | | | | | | 10.00 | | | (50) | 4 | 479 | | |
| PE-976 | 75.65 | 10.00 | 4.00 | 0.35 | | | | | 10.00 | | | (50) | 4 | 481 | 2 | |
| PE-978 | 80.00 | 10.00 | | | | | 10.00 | | | | | 75 | 4 | 440 | | 132 |
| PE-979 | 79.65 | 10.00 | | 0.35 | | | 10.00 | | | | | (67) | 4 | 566 | 126 | 234 |
| PE-980 | 86.00 | | 4.00 | | | | 10.00 | | | | | 75 | 2 | 350 | | 154 |
| PE-981 | 85.65 | | 4.00 | 0.35 | | | 10.00 | | | | | (61) | 1 | 503 | 153 | 218 |
| PE-982 | 76.00 | 10.00 | 4.00 | | | | 10.00 | | | | | (50) | 4 | 457 | | |
| PE-983 | 75.65 | 10.00 | 4.00 | 0.35 | | | 10.00 | | | | | (65) | 4 | 546 | 89 | |

◯ Note- Work Hardening level too high to allow continued processing without intermediate anneal

Figure 13C

| Alloy Code | Put-Up Composition, wt % | | | | | | | | | | | % CW | Edge* Cond. | Hardness | | UTS ksi |
|---|---|---|---|---|---|---|---|---|---|---|---|---|---|---|---|---|
| | Pd | Re | Ru | B | Pt | Ir | W | Au | Zr | Co | Ni | | | Hard. HK(100) | change with B addition | |
| PE-985 | 80.00 | 10.00 | | | | | | | | 10.00 | | 75 | 1 | 367 | | 165 |
| PE-986 | 79.65 | 10.00 | | 0.35 | | | | | | 10.00 | | 75 | 1 | 426 | 59 | 178 |
| PE-987 | 86.00 | | 4.00 | | | | | | | 10.00 | | 75 | 3 | 346 | | 166 |
| PE-988 | 85.65 | | 4.00 | 0.35 | | | | | | 10.00 | | 72 | 2 | 413 | 67 | 186 |
| PE-989 | 76.00 | 10.00 | 4.00 | | | | | | | 10.00 | | 75 | 4 | 406 | | 172 |
| PE-990 | 75.65 | 10.00 | 4.00 | 0.35 | | | | | | 10.00 | | 75 | 4 | 485 | 79 | 188 |
| PE-992 | 80.00 | 10.00 | | | | 10.00 | | | | | | 50 | 4 | 414 | | |
| PE-993 | 79.65 | 10.00 | | 0.35 | | 10.00 | | | | | | 72 | 4 | 488 | 74 | 151 |
| PE-994 | 86.00 | | 4.00 | | | | | | | | | 75 | 1 | 347 | | 153 |
| PE-995 | 85.65 | | 4.00 | 0.35 | | 10.00 | | | | | | 75 | 4 | 473 | 126 | |
| PE-996 | 76.00 | 10.00 | 4.00 | | | 10.00 | | | | | | 50 | 4 | 388 | | |
| PE-997 | 75.65 | 10.00 | 4.00 | 0.35 | | 10.00 | | | | | | 67 | 4 | 462 | 74 | 139 |
| PE-999 | 80.00 | 10.00 | | | | | | 10.00 | | | | 75 | 1 | 315 | | 192 |
| PE-1000 | 79.65 | 10.00 | | 0.35 | | | | 10.00 | | | | 67 | 1 | 460 | 145 | 105 |
| PE-1001 | 86.00 | | 4.00 | | | | | 10.00 | | | | 75 | 1 | 233 | | 138 |
| PE-1002 | 85.65 | | 4.00 | 0.35 | | | | 10.00 | | | | 75 | 1 | 360 | 127 | |
| PE-1003 | 76.00 | 10.00 | 4.00 | | | | | 10.00 | | | | 50 | 4 | 449 | | 119 |
| PE-1004 | 75.65 | 10.00 | 4.00 | 0.35 | | | | 10.00 | | | | 50 | 4 | 507 | 58 | 132 |
| PE-955 | 90.00 | | | | | | | | | | 10.00 | 75 | 1 | 281 | | 180 |
| PE-956 | 89.65 | | | 0.35 | | | | | | | 10.00 | 75 | 1 | 357 | 76 | 132 |
| PE-970 | 90.00 | | | | | | | | 10.00 | | | 75 | 1 | 459 | | 126 |
| PE-1010 | 89.65 | | | 0.35 | | | | | 10.00 | | | 75 | 4 | 486 | 27 | 192 |
| PE-977 | 90.00 | | | | | | 10.00 | | | | | 75 | 1 | 301 | | 114 |
| PE-1011 | 89.65 | | | 0.35 | | | 10.00 | | | | | 75 | 1 | 471 | 170 | 150 |
| PE-984 | 90.00 | | | | | | | | | 10.00 | | 75 | 1 | 274 | | 97 |
| PE-1012 | 89.65 | | | 0.35 | | | | | | 10.00 | | 75 | 1 | 380 | 106 | 171 |
| PE-991 | 90.00 | | | | | 10.00 | | | | | | 75 | 1 | 250 | | 66 |
| PE-1013 | 89.65 | | | 0.35 | | 10.00 | | | | | | 75 | 1 | 360 | 110 | 108 |
| PE-998 | 90.00 | | | | | | | 10.00 | | | | 75 | 1 | 162 | | 69 |
| PE-1014 | 89.65 | | | 0.35 | | | | 10.00 | | | | 75 | 1 | 288 | 126 | 140 |
| PE-963 | 90.00 | | | | 10.00 | | | | | | | 75 | 1 | 178 | | |
| PE-1009 | 89.65 | | | 0.35 | 10.00 | | | | | | | 75 | 1 | 336 | 158 | |

Note- Work Hardening level too high to allow continued processing without intermediate anneal

Figure 14

Increased Age Hardening Response when adding B to Pd-Ru-Re alloys

| Alloy code | Alloy Composition (wt%) | | | | %CW | Hardness Hk(100) | | Hardness increase after HT | Hardness increase from adding B (after HT) |
|---|---|---|---|---|---|---|---|---|---|
| | Pd | Re | Ru | B | | As cold worked | After 760F/60m HT | | |
| PE-942 | 83.00 | 15.00 | 2.00 | | 50 | 398 | 453 | 26 | |
| PE-952 | 82.65 | 15.00 | 2.00 | 0.35 | 50 | 362 | 522 | 160 | 134 |
| PE-943 | 76.00 | 20.00 | 4.00 | | AC | 481 | 487 | 6 | |
| PE-953 | 75.65 | 20.00 | 4.00 | 0.35 | 50 | 468 | 591 | 123 | 117 |
| PE-942 | 67.00 | 25.00 | 8.00 | | AC | 398 | 453 | 26 | |
| PE-954 | 66.65 | 25.00 | 8.00 | 0.35 | 45 | 486 | 549 | 63 | 37 |

…

PALLADIUM ALLOY

CROSS-REFERENCE TO RELATED APPLICATION

This application claims the benefit of U.S. Provisional Patent Application Ser. No. 60/569,671, filed May 10, 2004, which is incorporated herein by reference.

BACKGROUND OF THE INVENTION

1. Field of the Invention

The present invention relates generally to a metal alloy, and in particular, to an alloy including palladium, boron and one or more additional elements as solutes, and in particular to an alloy of palladium, boron and at least one of ruthenium, rhenium, iridium, platinum, tungsten, gold, zirconium, cobalt, nickel and tantalum. In an alternative embodiment, the alloy is of palladium and at least one of ruthenium and rhenium with an additional element chosen from iridium, platinum, tungsten, boron, gold, zirconium, cobalt, nickel and tantalum. The invention also relates to a product formed of the foregoing alloys.

2. Description of the Related Art

Platinum alloys, in particular, platinum-iridium alloys have been used in a wide variety of applications. Platinum-iridium alloys are widely used for both disposable and implantable medical devices to fabricate radio opaque marker bands for catheters, electrode rings, platinum alloy wires and coils, tubes, and machined components.

For example, radio opaque platinum-iridium alloys are used during medical procedures involving fluoroscope imaging since the radio opaque platinum-iridium alloy shows up very clearly in the fluoroscope image to thereby aid the medical personnel in performing their tasks.

The platinum-iridium alloy can also have a high yield strength or hardness along with well-established biocompatibility, which permits it to be used in implantable medical devices, such as pacemakers. The high yield strength also allows for the use of very fine wires that can accept a high torque loading during the steering of catheters or guide wires through small diameter blood vessels. The higher strength wires allow for a reduction in the wire diameter without a fear of breakage during use. Smaller diameter wires allow for access into finer blood vessels.

Platinum-iridium alloys are also popular for use in jewelry manufacturing due to its excellent white color and good hardness as well as its ability to be used in sheet stock, wire goods and investment casting. Platinum-iridium alloys have a higher melting temperature than gold alloys but can be investment cast or fabricated by cold working, hot working, and annealing, or soldering Another application is in space vehicle applications, thermocouples, electrical contacts, etc.

Platinum-iridium alloys are sold in varying proportions of platinum to iridium. For example, the common proportions are 90% platinum to 10%, iridium, referred to as 90:10 alloy, an alloy of 85% Pt-15% Ir, or 85:15, an alloy of 80% Pt to 20% Ir, or 80:20, an alloy of 75% Pt to 25% Ir, or 75:25, a 70:30 alloy, and even a 95:5 alloy.

In summary, platinum-iridium alloys are a mainstay in the medical market and are used for everything from guide wire tips and coils, due to the good radio opacity, to machined components and implantable pacemaker components. The jewelry trade uses the platinum-iridium alloys due to their combination of strength and resistance to tarnish and oxidation. The platinum-iridium alloys provide a combination of strength and biocompatibility.

However, the price of platinum has reached record levels, recently exceeding $900 per ounce, which is three times the current cost of palladium. This places significant economic strains on the continued use of high platinum alloys.

SUMMARY OF THE INVENTION

The present invention provides an alloy family sharing many of the characteristics of platinum-iridium alloys and is foreseeable as a lower cost replacement for platinum-iridium alloys. The present invention provides a family of alloys based on palladium and boron with an additional component. The additional component is one or more of the elements chosen from the following; ruthenium, rhenium, iridium, platinum, tungsten, gold, zirconium, cobalt, nickel and tantalum. In a further embodiment of the invention, the alloy is of palladium and one or both of ruthenium and rhenium with an additional component chosen from the following: iridium, platinum, boron, tungsten, gold, zirconium, cobalt, nickel and tantalum. According to a further aspect, the invention relates to a product formed of the foregoing alloys.

In a preferred embodiment, the additional component is one of ruthenium or rhenium or may be both ruthenium and rhenium. In one example of the preferred embodiment, the palladium component is in a range of 45% to 99.95%, the ruthenium component is in a range of 0% to 8%, the rhenium component in the range of 0% to 25% (with the sum of the Ru and Re components generally exceeding 1%) and the boron component in a range from 0.005% to 1.5%. Additional additives may be present in the alloy as well.

In second preferred embodiment, the additional component may be one or more of the following additives: platinum or gold in the range of O to 30%, rhenium in the range of O to 25%, zirconium, tungsten, cobalt, nickel, tantalum or iridium in the range of 0 to 15%, ruthenium in the range of 0 to 8%, and boron in the range of 0.005 to 1.5% (with the sum of the boron plus all the other solutes generally exceeding 0.5%).

BRIEF DESCRIPTION OF THE DRAWINGS

FIG. 3 is a table of palladium alloys assigned a sequence number and showing constituents and characteristics;

FIG. 4 is a table of testing results for various alloys of the sequence of FIG. 3 at various annealing temperatures;

FIG. 5 is a table of strip and wire characteristics of some alloys of FIG. 3;

FIG. 6 is a table of strip test results for some alloys showing the effect of boron on a palladium alloy with 4.5% ruthenium;

FIG. 7 is a table of strip test results for some alloys showing the effect of cold work on the mechanical properties of selected alloys;

FIG. 8 is a table of radio opacity data for some alloys of FIG. 3 along with text describing the test conditions FIG. 9 is a table of three alloy compositions used in biocompatibility testing;

FIG. 10 is a table showing the results of biocompatibility testing for a first of the alloys in FIG. 9;

FIG. 11 is a table showing the results of biocompatibility testing for a second of the alloys in FIG. 9;

FIG. 12 is a table showing the results of biocompatibility testing for a third of the alloys in FIG. 9;

FIGS. 13A, 13B and 13C are tables showing put ups for various alloys in the present alloy family and the characteristics thereof;

FIG. 14 is a table showing the effect of boron on the age hardening response for selected alloys.

DETAILED DESCRIPTION OF THE PREFERRED EMBODIMENTS

Figure 1:
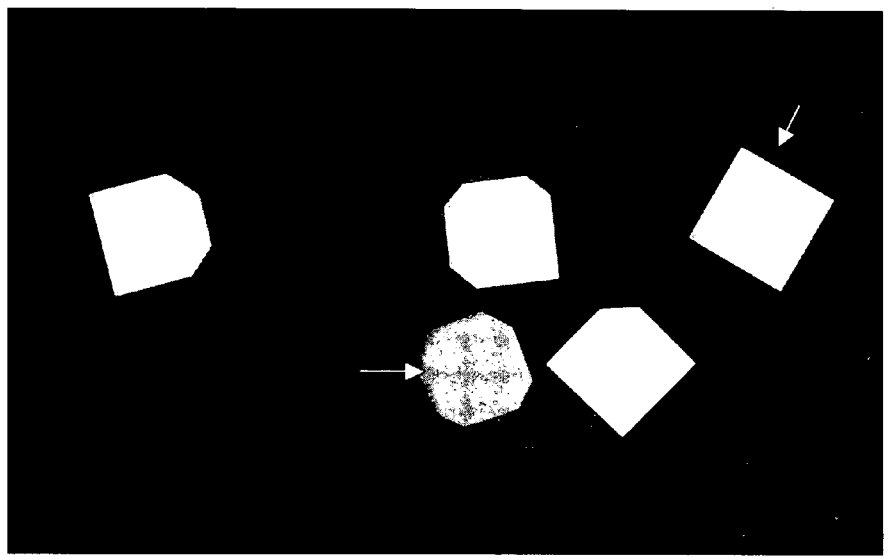
FIG. 1 is a radiograph showing radio opacity of alloys according to the principles of the present invention in comparison to stainless steel and a platinum iridium alloy at 50 KV.

In this document, the percentages of the alloy components refer to weight percent.

In the broadest sense, the present alloy is an alloy of palladium and boron with an additional element chosen from the following: ruthenium, rhenium, iridium, platinum, tungsten, gold, zirconium, cobalt, nickel and tantalum, or alternatively is an alloy of palladium and one or both of rhenium and ruthenium with an additional element chosen from the following: iridium, platinum, boron, tungsten, gold, zirconium, cobalt, nickel and tantalum. In one preferred embodiment, the alloy includes palladium and boron and at least one of ruthenium and rhenium. An exemplary embodiment has proportions of palladium (Pd) in the range of 45% to 99.95%, ruthenium (Ru) in the proportion of 0% to 8%, rhenium (Re) in the range of 0% to 25%, and boron (B) in the proportion of 0.005% to 1.5%. The ruthenium and rhenium components can be both present in the alloy, or the alloy may be formed with only one of these elements. In addition, additives may be included as follows:

Platinum (Pt) up to 30%,
Gold (Au) up to 30%,
Zirconium (Zr) up to 15%,
Tungsten (W) up to 15%,
Cobalt (C) up to 15%,
Iridium (Ir) up to 15%,
Nickel (N) up to 15%, and
Tantalum (Ta) up to 15%.

Within this broad family of alloys are at least six different subcategories:

Pd—Ru—B, with or without additives;
Pd—Re—B, with or without additives;
Pd—Ru—Re—B, with or without additives;
Pd—B alloys, with one or more of the following additives Re, Ru, Zr, Co, Ir, Ni, Ta, Au, Pt, and W.
Pd—Re alloys with one or more of the following additives B, Ru, Zr, Co, Ir, Ni, Ta, Au, Pt, and W.
Pd—Ru alloys with one or more of the following additives B, Re, Zr, Co, Ir, Ni, Ta, Au, Pt, and W.

The scope of this invention is not limited to the foregoing list of additives, but may include others.

The resulting alloys are capable of gaining additional strength due to a heat treating step, making use of an age hardening reaction.

The present alloys have a number of characteristics that make it a viable replacement for expensive platinum-iridium alloys, including a high degree of radio opacity (radiopaque), high strength, lower density, biocompatibility, and a lower cost. Each of these will be addressed in the following. The present alloy is ideally suited as a medical radiopaque marker, a medical lead, an implant component, electrodes, or a guidewire tips or coils. The alloy may be used in catheters, for example as radiopaque markers, coils or feed-through components.

For use in the body, the alloy must be biocompatible. Three families of alloys according to this disclosure, namely the Pd—Ru—B alloy, the Pd—Re—B alloy, and the Pd—Ru—Re—B alloy, have all been tested for biocompatibility and all three have passed a battery of five tests. Details of the biocompatibility tests are set forth in FIGS. 9, 10, 11 and 12, as will be described in greater detail hereinafter.

The alloy families of the present invention provide a potential savings of hundreds of dollars per ounce compared to commercial platinum-iridium alloys. Thus, a first cost saving aspect is due to the lower cost components. The present alloys have a lower density level than the platinum-iridium alloys so that each ounce of material provides a larger volume of material while still providing a strength generally equivalent to, and in some cases exceeding that, of 90% platinum-10% iridium alloys. The lower density is a second cost saving aspect. The type and proportion of added elements can vary the density of the alloy. However, density levels for the alloys within the scope of this invention offer densities that are 20% to 50% lower than a 90% platinum-10% iridium alloy.

The high strength palladium-boron plus additive alloys envisioned by this invention provide improved mechanical properties and processing characteristics verses conventional palladium-ruthenium casting alloys used in some jewelry alloys. The strength of the material is important for many applications, particularly for in-body applications. The present alloy has excellent strength characteristics. The mechanical properties are reported in tables described hereinbelow.

Various alloys in the present alloy family have been prepared and tested. In the processing of these alloys, alternating steps of cold working, typically followed by an annealing step, is performed. At the end of the processing sequence, the cold working is often followed by a stress relief annealing step for improved ductility. The resulting alloy has a high strength in combination with good formability. The cold working has been performed with a 50% cold working, and with 75% cold working which yields an even harder alloy. For example, the hardness of an embodiment of the alloy before and after cold working by 75% changed from 134 to 270 Knoop. A similar change is seen in a further embodiment of 265-400 Knoop. The processing and resulting characteristics is reported in the accompanying tables.

In general, a four element alloy version (Pd—Ru—Re—B) of the present invention provides the same strength level as the 90-10 platinum-iridium alloy at half the total solute content. As noted herein, three element alloy versions (also referred to a ternary alloys) (Pd—Ru—B or Pd—Re—B) also provide excellent replacement possibility for the platinum-iridium alloys. The present alloy system provides high strength levels without a loss of processability.

In particular applicants have found, surprisingly, that synergies exist when boron is added to the ruthenium and/or rhenium containing alloys. For example, while alloys 933 and 938 as shown in FIG. 13A differ by only about 0.35% boron, the addition of boron resulted in a doubling of cold worked hardness while maintaining surprising ductility. Similar increases in cold hardness is seen for many of the paired alloys showed in FIGS. 13A, 13B and 13C.

For example, applicants have discovered boron shows the same marked synergy when rhenium is present without ruthenium. Comparison of alloys 897 and 893 demonstrate this synergy. The addition of only about 0.35% boron to a 10% rhenium containing alloy caused an increase in cold worked hardness from Knoop 319 without the boron to Knoop 477 with boron added.

An increase in solute levels of Re in the alloy to about 11% has provided very strong alloys.

Applicants have also found, and disclosed in the tables, and in particular in FIGS. 3-13, that the proportions of ruthenium, rhenium and boron in these alloys can be varied such that alloys having more boron require less ruthenium and/or rhenium to reach the same hardness levels.

As noted herein, applicants have further discovered that additions of other elements further add to the remarkably high strength and ductility of these alloy families. By way of demonstrating these effects, when applicants added 10% of tungsten to Alloy 917, thereby creating alloy 981 applicants increased the cold worked hardness from Knoop 423 to Knoop 503, without sacrificing ductility. Having ductility at such high hardnesses has not, as far as applicants know, been reported for other alloys containing either platinum or palladium as their major constituents. By ductility in the foregoing examples, applicants refer to the condition of the edge of the strip samples as they are rolled, or wrought, down to thinner thicknesses such that the high hardness achieved by cold working was not accompanied by edge defects as those skilled in the art would expect to find while trying to cold work alloys of such high hardnesses.

To put the above increases of hardness into clearer perspective, tests done on the binary combinations of these elements do not reach these extreme hardness values. For example, alloy 925, consisting of palladium plus 0.35% boron added had a cold worked hardness of only Knoop 270 at 75% CW. Similarly an alloy, alloy 935, consisting of palladium plus 4.0% ruthenium had a cold worked hardness only Knoop 208 at 75% CW level. Likewise an alloy consisting of palladium plus 5% rhenium, alloy 887, had a cold worked hardness of only Knoop 265 with 75% CW.

The attached tables include a FIG. 3 showing alloys numbers 844 through 884, and identify the constituent components as well as the percentage of elongation and hardness results from testing at 50% cold work. Boron content in these specifications refers to the proportion of boron added during initial alloying, not to the proportion of boron found in the finished alloy. Due to the poor efficiency of capturing boron additions in the molten metal, a retention of only about 20% to 60% of the quantity originally added during alloying is found.

FIG. 4, identified as short term thermal tests, shows short term heat treatment tests for alloys No.880, 882, and 883, each of which have been cold worked to two different percentages of cold work. The results of the hardness testing are shown both before and after the heat treatment. For all three alloys the hardness increase with thermal exposure showing initial evidence of an age hardening response. The response in more pronounced with increased cold work prior to aging.

FIG. 5 illustrates the properties of the alloy 852 that has been formed into a strip and into a wire, contrasting the strip verses wire properties, including the benefits of a stress relief anneal to provide a significant increase in elongation.

FIG. 6 presents the test results for alloys 846 and 851-853 illustrating the effect of increased boron in a Pd-4.5% Ru alloy.

FIG. 7 presents test results for alloys 877 to 886, and illustrates the significant increase in mechanical properties for cold work factors over 50%.

FIG. 8 describes the radiopacity trials done on selective alloys according to the invention. The testing reveals a high degree of radiopacity for the embodiments of the invention. The test conditions are as follows. X-ray testing was done in radiographic laboratory (using standard equipment). All the metal samples were 0.009 inches thick. The initial (50 KV) tests used conventional settings for extremity cassette exposure. Exposures were also done at increased X-ray tube voltages. This acts to increase the penetrating power of the x-ray and makes it harder to detect the stainless steel sample. However, both the 90Pt-10Ir sample and alloys 847, 879 and 883 according to this invention were easy to see over all test conditions used. The stainless steel and 90Pt-10IR coupons are included as comparison standards.

A key characteristic of the platinum-iridium alloys which should be found in a viable replacement is that of radio opacity. Since radio opacity tends to follow density, the densities of the present alloys have good radio opacity for most applications. In particular, the present alloy is denser than stainless steel and thus will be more radio opaque than stainless.

A common belief is that the radiopacity of material is a cubic function of the atomic number. The atomic number of platinum is 78 and the atomic number of palladium is 47, yet the tests have revealed a surprising result in that the present alloys are nearly as radio opaque as the platinum-iridium alloys. The FIG. 8 and following figures demonstrate the radiopacity of these alloys compared to 17-4 PH stainless steel and 90% platinum-10% iridium.

Figure 2:
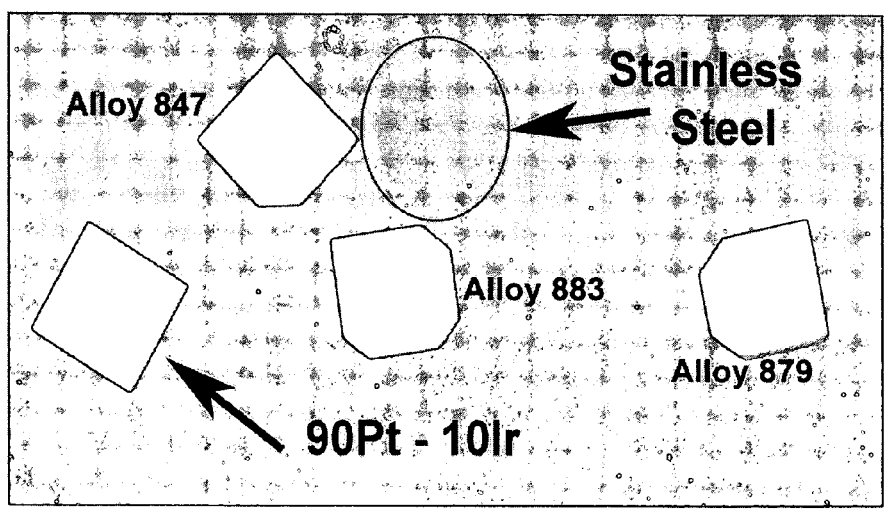
FIG. 2 is a radiograph showing radio opacity of alloys according to the principles of the present invention in comparison to stainless steel and a platinum iridium alloy at 60 KV.

FIGS. 1 and 2 show two of the actual radiographs described in FIG. 8. The samples of the present alloy have one, two or three corners cut off and the comparison sample of stainless steel has four corners cut off, while a comparison sample of Pd-Ir has no corners cut off. In FIG. 1, the test has done with samples of the alloys 847, 879 and 883 and with stainless steel and a 90:10 platinum-iridium alloy for comparison. The samples were all prepared to a thickness of 0.009 inches in thickness and were x-rayed in a standard x-ray machine of with the x-ray tube voltage set at 50 Kv. The stainless steel sample has a low radiopacity by comparison, whereas the platinum-iridium sample has a high radiopacity. The alloys of the present invention also have a high radiopacity, approaching that of the platinum-iridium sample.

In FIG. 2, the tube voltage was increased to 60 Kv to increase the penetration of the x-rays. The stainless steel sample nearly disappears but the present alloys, 847, 879 and 883, and the platinum-iridium sample have a high degree of radiopacity. In the view of FIG. 2, the background has been lightened to show the location of the stainless steel sample, which would otherwise not be apparent.

Densitometer measurements of the film was done after exposure to the x-rays at various tube voltages. At 50 Kv, the stainless steel has a rating of 0.66, the three alloys 847, 879 and 883 each have ratings of 0.20, and the Pd-Ir alloy has a rating of 0.20. At a tube current of 60 Kv, the stainless steel sample rating is 2.17, the three alloys samples 847, 879 and 883 are rated at 0.25, 0.23 and 0.24, respectively, and the P1-Ir sample is 0.22. A further increase of the tube current to 70 Kv results in a measured rating for the stainless steel sample at 3.28, for the three alloys 847, 879 and 883 at 0.72, 0.62 and 0.66, respectively, and for the Pd—Ir sample at 0.39.

Uses of the present alloy family include in medical devices including radio opaque medical devices, machined medical devices and implantable medical devices. In addition, the present alloy may readily be used in electrical contact applications, the jewelry market and other applications requiring high strength, high hardness and good tarnish resistance. The present alloys are particularly advantageous as low noise signal contacts and may be used as either sliding electrical contacts or static electrical contacts.

The present alloy is seen as a replacement for 90:10 platinum-iridium alloys as well as 85:15 platinum-iridium alloys and may replace 80:20 platinum-iridium alloys in some applications. Mechanical testing has been carried out on the alloys of this alloy family and the results are set forth in the tables. The strength data included testing of the raw alloys, testing after cold working in various percentages and after annealing for stress relief at various temperatures. For example, cold working has been carried out at 50% and at 75%, with a higher strength product seen after the 75% cold working.

The thermal exposure data in FIGS. 3 and 14 indicate that for some of the alloys within this family, higher strength and hardness levels are achievable though the use of a post form heat treatment.

Particularly high strength and hardness values are seen, for example, in alloys 880, 882, and 883 wherein the strength, measured in the Knoop hardness scale increases significantly after stress relief annealing. In particular, see alloy No. 883. Referring to the table of alloys in the alloy family, alloy No. 883 has proportions of palladium of 90.15%, ruthenium of 4.5%, and boron of 0.35% and 5% rhenium. The percentage of rhenium may extend up to 20%, as may be determined by reference to a palladium rhenium binary phase diagram. The alloy No. 883 reached a Knoop hardness level of 503, after a short term aging anneal following 66% cold work, thus holding particular promise. This increasing hardness when held at an intermediate temperature suggests that some of the alloys in this family undergo an age hardening or ordering reaction. This is further illustrated in FIG.14.

Thus, the strength of the present alloy families has been shown. The present alloy family has proven to be biocompatible as well. In general, members of the platinum group metals are biocompatible. Although rhenium is a refractory metal, it shares many of the physical, chemical, and mechanical characteristics of the platinum group elements, and this element is known to have good biocompatibility and osteoconductivity characteristics.

In FIG. 9 is a listing of alloys 847, 900 and 902, the components of which are shown in the table, that have been formed into strips and wires and tested for biocompatibility. The three alloys passed five biocompatibility tests, including: 1) cytotoxicity using the ISO elution method, 2) ISO intracutaneous testing using aqueous and organic extraction, 3) ISO systemic toxicity testing using aqueous and organic extraction, 4) ISO muscle implant for two weeks, and 5) in vitro hemolysis using aqueous extraction (a modified ASTM process). ASTM=American Society for Testing and Materials.

FIGS. 10, 11 and 12 show the specific testing results for each of the alloys 847, 900 and 902, respectively, in the form of a test matrix. The results show excellent biocompatibility for these materials.

Testing as to formability of the present alloy family suggests that they may be formed into spring coils and the like without cracking, which is surprising for materials of such high hardness.

FIGS. 13A, 13B and 13C show examples of alloys, including alloys 924 through 1014. In most cases, the alloys are paired together to show the increased mechanical properties that occur with small additions of boron. The alloy put up compositions are shown as is information on hardness, tensile strength and processability. In some cases, the alloys work hardened to such a degree that additional reductions exceeded the hold down force of the rolling mill. These cases are shown with circles around the resultant cold work percentage.

FIG. 14 shows the age hardening response of the alloys 948, 952, 953 and 954 which shows the hardness results for three boron containing alloys with higher solute levels. All of these alloys achieved hardness levels above 500 Hk(100) after aging. As in cold work cases shown in FIGS. 13A-13C, the addition of the B (boron) greatly enhanced the final hardness.

The data presented in the tables also reveals that alloys of palladium with rhenium and an additional component and alloys of palladium with ruthenium and an additional component have a characteristics which make them a viable and valuable replacement for the platinum-iridium alloys of the prior art. In particular, such palladium and either rhenium or ruthenium based alloys with an additional component have tested to a high strength. These palladium and either ruthenium or rhenium based alloys are presented as alloy numbers 994, 980, 971 and 957 in the tables. Testing of these alloys has revealed a shortcoming for these embodiment, in that there is a lack of ductility. However, the reduced ductility characteristic is less important in casting alloys and so it is foreseen that these alloys may be used in cast products. It is also foreseeable that further anneals for processing these alloys may increase the ductility characteristic, although testing of such further processing has not yet been completed.

Thus, there is disclosed an alloy which is a viable replacement to platinum iridium alloys while providing a lower cost and meeting the significant characteristics of the more expensive known alloy. The present alloy family includes alloys with varying ranges of components and various additives as noted above. These alloys may be used in medical applications, where they are worked and annealed and may be formed into strips or wires, or tubes, or coils, or into machined components. In addition, it is foreseen that the present alloy family may find applications as sliding electrical contact materials (where high hardness and tarnish resistance is required), utility in cast jewelry (rather than worked metal), or may be utilized in various other application where the advantageous characteristics of this alloy family are required.

The examples presented hereinbelow represent the current optimization of embodiments. However, further changes, additions or deletions may also be possible and are within the scope of this invention.

EXAMPLES OF PREFERED EMBODIMENTS

Within the broad families of alloys that are within the scope of this invention are a number of more preferred compositions that are ideally suited to particular applications. For instance, a preferred alloy of a first embodiment has a balance of Pd (palladium)—about 10.5% Re (rhenium)—and about 0.08% B (boron) nominal. The ranges of the components for this first embodiment are: Re (rhenium) 10.5% plus or minus 0.5%—B (boron) 0.08% plus or minus+0.05%—and a balance of Pd (palladium). This embodiment has attributes of low cost, low density, biocompatible (similar to PE 902), good radiopacity, and high strength. The potential uses for this alloy include use as catheter coils; trails indicate coiling characteristics similar to Pt—Ni and Pt—W alloys.

An alloy according to the first embodiment, which is referred to in the tables as alloy 100, has been formed into wires with diameters between 0.0025 inch and 0.010 inch. The alloy is provided in two grades, a standard grade and a medical grade. The standard grade has a balance of Pd, 10 to 11% Re, 0.03 to 0.13 B, a maximum of 1000 ppm for each of Rh, Pt, Ru, Os, Au and Ag, and a maximum of 0.2% of other ingredients. The medical grade has a balance of Pd, 10 to 11% Re, 0.03 to 0.13 B, a maximum of 1000 ppm for each of Rh, Pt, Ru, Os, Au and Ag, a total of 30 ppm maxium for Pb, As, Bi and Cd, a maximum 100 ppm for Cu, a maximum 75 ppm for Ni, a maximum 100 ppm for Fe, and a maximum 500 ppm for other ingredients excluding Rh, Pt, Ru, Os, Ag and Au, with a maximum 200 ppm for all other elements. For a wire according to this embodiment of a diameter of 0.002 inches to 0.015 inches, a stress relieved strength (UTS) of 180 to 235 ksi has been achieved for an elongation of 2.5% minimum in 10 in gauge length.

In this first embodiment, the primary solutes are Pd, Re and B. The component Ru can be treated as a potential additive In a second embodiment, the alloy has a balance of Pd—about 5% Re—and about 0.08% B nominal. The ranges for the components are Re 5% plus or minus 0.5%—B 0.08% plus or minus 0.05% and a balance of Pd. This embodiment has attributes of low cost, low density, biocompatible, good radiopacity, and moderate strength.

In a third embodiment, the alloy has a balance of Pd—about 10% W—about 4% Ru—and about 0.08% B nominal. The components of this embodiment are in a range of W 10% plus or minus 0.5%—Ru 4% plus or minus 0.5%—B 0.08% plus or minus 0.05% and a balance of Pd. The attributes of this embodiment are low cost, low density, very high hardness with good processability, good radiopacity, and high strength.

In a fourth embodiment, the alloy has a balance of Pd—about 20% Re—about 4% Ru—and about 0.08% B nominal. The components of this embodiment are in a range of Re 20% plus or minus 1%—Ru 4% plus or minus 0.5%—B 0.08% plus or minus 0.05% and a balance of Pd. The attributes of this alloy are low cost, low density, good radiopacity, high strength, and an age hardenable system capable of reaching hardness level of nearly 600 Hk.

In a fifth embodiment, the alloy has a balance of Pd—about 2% Ru—and about 0.08% B nominal. The ranges are Ru 2% plus or minus 0.5%—B 0.08% plus or minus 0.05% and a balance of Pd. The attributes are low cost, low density, good radiopacity, and moderate strength.

The benefits of all these alloys—low density with unexpected high strength and high radiopacity. Also much lower cost that Pt alloys—two fold benefit—lower intrinsic value for Pd verses Pt (currently a factor of nearly 4 to 1), and lower density gives additional benefit of more material per oz. Radiopacity is unexpected since at Kev (x-ray energy level) of interest here—we were told radiopacity should be a cubic function of the atomic number (Pd is 47 and Pt is 78), and yet as shown in the provisional patent application these alloys are very close to Pt—Ir alloys.

Although other modifications and changes may be suggested by those skilled in the art, it is the intention of the inventors to embody within the patent warranted hereon all changes and modifications as reasonably and properly come within the scope of their contribution to the art.

We claim:

1. An alloy comprising three primary elements as follows:
a first primary element Pd as a balance of the alloy;
a second primary element Re in a range of 10.5 wt % ±0.5 wt %; and
a third primary element B in a range of 0.08 wt % ±0.05 wt %.

2. A palladium-based alloy, consisting of:
palladium and boron in a range of 0.005 to 1.5 weight percent and rhenium in a range of 3 to 20 weight percent,
said palladium-based alloy being formed into a device.

3. A palladium-based alloy, consisting of:
palladium and boron in a range of 0.005 to 1.5 weight percent and rhenium in a range of 3 to 20 weight percent,
and at least one trace element,
said palladium-based alloy being formed into a device.

* * * * *